US011452814B2

(12) United States Patent
Montalvo et al.

(10) Patent No.: US 11,452,814 B2
(45) Date of Patent: *Sep. 27, 2022

(54) AMBULATORY INFUSION DEVICES AND FILTER ASSEMBLIES FOR USE WITH SAME

(71) Applicant: MEDTRONIC MINIMED, INC., Minneapolis, MN (US)

(72) Inventors: Susan McConnell Montalvo, Woodland Hills, CA (US); Rudolph A. Montalvo, Woodland Hills, CA (US); Milton Stott, Camarillo, CA (US); Darren Y. K. Yap, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/888,749

(22) Filed: May 31, 2020

(65) Prior Publication Data

US 2020/0297923 A1    Sep. 24, 2020

Related U.S. Application Data

(63) Continuation of application No. 15/823,351, filed on Nov. 27, 2017, now Pat. No. 10,668,209.

(Continued)

(51) Int. Cl.
*A61M 5/142*    (2006.01)
*A61M 5/165*    (2006.01)
(Continued)

(52) U.S. Cl.
CPC ........ *A61M 5/14244* (2013.01); *A61M 5/145* (2013.01); *A61M 5/14248* (2013.01);
(Continued)

(58) Field of Classification Search
CPC ............ A61M 5/1407; A61M 5/14244; A61M 5/145; A61M 5/165; A61M 2005/1406;
(Continued)

(56) References Cited

U.S. PATENT DOCUMENTS 2,248,006 A * 7/1941 MacCallum, Jr. ...... G01F 23/16
73/303
4,395,260 A    7/1983 Todd et al.
(Continued)

FOREIGN PATENT DOCUMENTS

EP    142866 A2    5/1985
EP    0586740 A1    3/1994
(Continued)

OTHER PUBLICATIONS

PCT International Search and Written Opinion dated May 4, 2018 for PCT App. Ser. No. PCT/US2017/063319.
(Continued)

*Primary Examiner* — Jason E Flick
(74) *Attorney, Agent, or Firm* — Foley & Lardner LLP (57) ABSTRACT

An ambulatory infusing device including a housing, a reservoir defining an interior volume, a wall associated with the housing and having an inner surface that faces into the reservoir interior volume, and a filter assembly. The filter assembly may include a filter assembly housing with a housing filter portion having a filter supporting volume, a filter located within the filter supporting volume, and a bubble guard, including a bubble guard wall and at least one bubble guard aperture that extends through the bubble guard wall, associated with the filter assembly housing such that the bubble guard wall is located in spaced relation to the filter.

20 Claims, 8 Drawing Sheets

Related U.S. Application Data (60) Provisional application No. 62/452,637, filed on Jan. 31, 2017.

(51) Int. Cl.
| | |
|---|---|
| *A61M 5/145* | (2006.01) |
| *A61M 5/38* | (2006.01) |
| *A61M 5/36* | (2006.01) |
| *A61M 5/14* | (2006.01) |
| *A61M 5/168* | (2006.01) |
| *A61M 5/158* | (2006.01) |

(52) U.S. Cl.
CPC .............. *A61M 5/165* (2013.01); *A61M 5/36* (2013.01); *A61M 5/38* (2013.01); *A61M 5/1407* (2013.01); *A61M 5/14212* (2013.01); *A61M 5/158* (2013.01); *A61M 5/16854* (2013.01); *A61M 2005/1406* (2013.01); *A61M 2205/18* (2013.01)

(58) Field of Classification Search
CPC .......... A61M 2205/18; A61M 5/14212; A61M 5/14248; A61M 5/158; A61M 5/16854; A61M 5/36; A61M 5/38; A61M 5/14; A61M 5/142; A61M 5/14276; A61M 2005/14513; A61M 5/14586; A61M 5/14593; A61M 2005/1657; A61M 5/14224; A61M 5/16831; A61M 5/365
See application file for complete search history.

(56) References Cited

U.S. PATENT DOCUMENTS

| | | | |
|---|---|---|---|
| 4,573,994 A | 3/1986 | Fischell et al. | |
| 4,714,462 A | 12/1987 | DiDomenico | |
| 4,718,893 A | 1/1988 | Dorman et al. | |
| 4,743,371 A * | 5/1988 | Servas | A61M 1/3627 96/179 |
| 4,772,263 A | 9/1988 | Dorman et al. | |
| 4,838,887 A | 6/1989 | Idriss | |
| 4,955,861 A | 9/1990 | Energren et al. | |
| 5,088,983 A | 2/1992 | Burke | |
| 5,417,663 A * | 5/1995 | Slettenmark | A61M 5/14276 604/126 |
| 5,471,663 A | 5/1995 | Slettenmark | |
| 5,957,890 A | 9/1999 | Mann et al. | |
| 6,361,780 B1 * | 3/2002 | Ley | A61M 31/002 424/443 |
| 8,740,861 B2 | 6/2014 | McConnell et al. | |
| 10,668,209 B2 | 6/2020 | Montalvo et al. | |
| 10,675,403 B2 | 6/2020 | Montalvo et al. | |
| 2002/0087147 A1* | 7/2002 | Hooper | A61M 5/141 604/892.1 |
| 2009/0264870 A1 | 10/2009 | Christenson | |
| 2010/0274196 A1 | 10/2010 | Brandt et al. | |
| 2011/0190688 A1 | 8/2011 | Tagliaferri et al. | |
| 2014/0228806 A1 | 8/2014 | Alisantoso et al. | |
| 2016/0095987 A1* | 4/2016 | Chattaraj | A61M 5/14244 604/126 |
| 2018/0214632 A1 | 8/2018 | Montalvo et al. | |
| 2020/0390970 A1 | 12/2020 | Montalvo et al. | |

FOREIGN PATENT DOCUMENTS

| | | |
|---|---|---|
| EP | 0790070 A1 | 8/1997 |
| WO | WO-96/40357 A1 | 12/1996 |

OTHER PUBLICATIONS

Extended European Search Report dated Nov. 23, 2021, from application No. 21199566.7.
U.S. Non-Final Office Action dated Feb. 16, 2022, from U.S. Appl. No. 16/888,744.
U.S. Notice of Allowance dated Jun. 7, 2022, from U.S. Appl. No. 16/888,744.

* cited by examiner

AMBULATORY INFUSION DEVICES AND FILTER ASSEMBLIES FOR USE WITH SAME

CROSS-REFERENCE TO RELATED APPLICATION

This application is a continuation of U.S. application Ser. No. 15/823,351, filed Nov. 27, 2017, which claims the benefit of U.S. Provisional Application No. 62/452,637, filed Jan. 31, 2017, which is incorporated herein by reference.

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") in accordance with a delivery profile that specifies one or more flow rates during the delivery profile cycle, and frequently include a reservoir and a fluid transfer device. The reservoir is used to store the infusible substance and is coupled to the fluid transfer device which is, in turn, connected to an outlet port. A catheter, which has at least one outlet at the target body region, may be connected to the outlet port. As such, infusible substance in the reservoir may be transferred from the reservoir to the target body region by way of the fluid transfer device and catheter.

SUMMARY

An infusion device in accordance with at least one of the present inventions includes a housing, a reservoir defining an interior volume, a divider wall associated with the housing and having an inner surface that faces into the reservoir interior volume, and a filter assembly. The filter assembly may include a filter assembly housing with a housing filter portion having a filter supporting volume, a filter located within the filter supporting volume, and a bubble guard, including a bubble guard wall and at least one bubble guard aperture that extends through the bubble guard wall, associated with the filter assembly housing such that the bubble guard wall is located in spaced relation to the filter. There are a variety of advantages associated with such an infusion device. By way of example, but not limitation, the bubble guard prevents bubbles from reaching the volume adjacent to the filter. As such, the infusion device will be functionally effective when there are air bubbles in the infusible substance.

An infusion device in accordance with at least one of the present inventions includes a housing, a reservoir defining an interior volume, a divider wall associated with the housing and having an inner surface that faces into the reservoir interior volume, and a filter assembly. The filter assembly may include a filter assembly housing with a housing filter portion having a side wall and an end wall that define a filter supporting volume, a filter located within the filter supporting volume, and at least one side wall aperture that extends through the side wall to the filter supporting volume. There are a variety of advantages associated with such an infusion device. By way of example, but not limitation, the side wall aperture allows infusible substance to flow under bubbles that are adjacent to the filter. As such, the infusion device will be functionally effective when there are air bubbles in the infusible substance.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions have application in a wide variety of apparatus. One example is an electromagnet-pump-based fluid transfer device that may be employed in an implantable infusion device. The present inventions are not, however, limited to electromagnet-pump-based fluid transfer devices and implantable infusion devices and are instead also applicable to other fluid transfer devices and infusion devices that currently exist, or are yet to be developed. For example, the present inventions are applicable to fluid transfer devices with solenoid pumps or any other pump that delivers a known and non-adjustable volume into a compliant volume.

Figure 1:
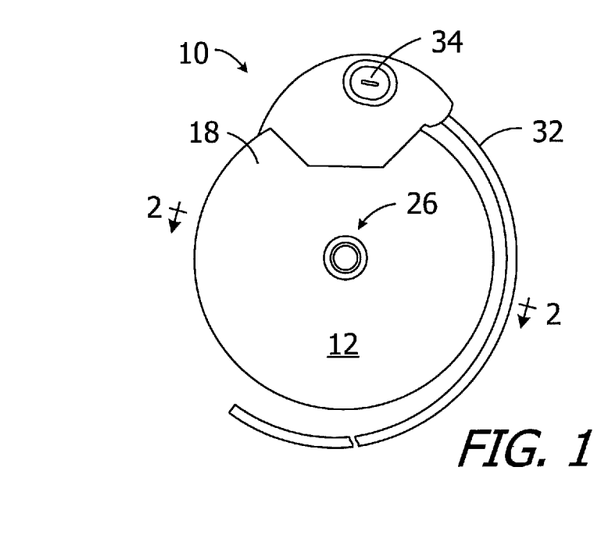
FIG. 1 is a front view of an implantable infusion device.
Figure 2:
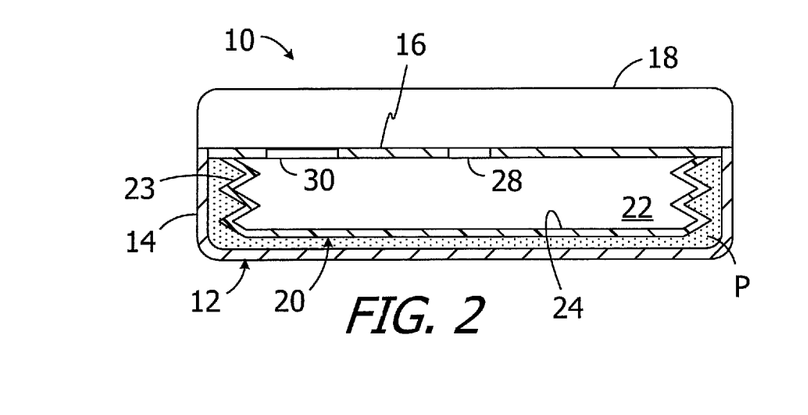
FIG. 2 is a partial section view taken along line 2-2 in FIG. 1.

One example of an infusion device is illustrated in FIGS. 1 and 2. The infusion device 10 includes a housing 12 (e.g. a titanium housing) with a bottom portion 14, an internal wall 16, and a cover 18. A reservoir 20 is located within the housing bottom portion 14 and an infusible substance (e.g. medication) may be stored in the reservoir internal volume 22. A wide variety of reservoirs may be employed. In the illustrated embodiment, the reservoir 20 is in the form of a titanium bellows, with convolutes 23 and an end wall 24, that is positioned within a sealed volume defined by the housing bottom portion 14 and internal wall 16. The remainder of the sealed volume is occupied by propellant P, which may be used to exert negative pressure on the reservoir 20. The reservoir 20 may be replenished by way of a fill port 26 that extends through the housing cover 18 and is connected to a reservoir inlet 28. A hypodermic needle (not shown), which is configured to be pushed through the fill port 26, may be used to replenish the reservoir 20. A safety valve (not shown) that is configured to close when the pressure within the internal volume 22 reaches a predetermined level may be located between the fill port 26 and the reservoir inlet 28. The fluid transfer device and various electronic components (not shown) are located within a sealed volume defined by the housing internal wall 16 and cover 18. The inlet of the fluid transfer device is coupled to the reservoir internal volume 22 by way of a filter assembly 30 that blocks pathogens and precipitates which may be in the infusible substance. The outlet of the fluid transfer device is operably connected to a catheter 32. Access to the catheter 32 may also be obtained by way of a catheter access port 34.

Figure 3:
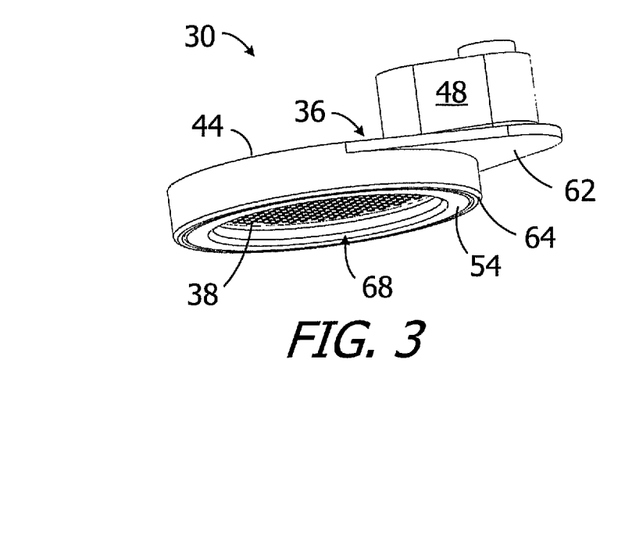
FIG. 3 is perspective view of the filter assembly in the implantable infusion device illustrated in FIG. 1.
Figure 4:
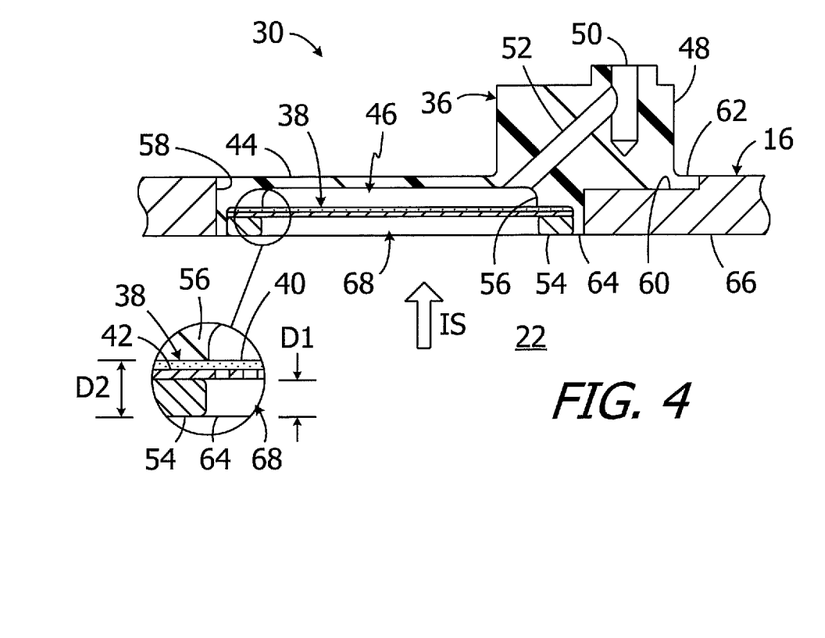
FIG. 4 is a section view of a portion of the implantable infusion device illustrated in FIG. 1.

Turning to FIGS. 3 and 4, the filter assembly 30 includes a housing 36 and a filter 38 having a bacterial filtration element 40 and a perforated support disk 42 that prevents distortion of the filter element. The filtration element 40 may be a pathogen-blocking bacterial filtration element formed from hydrophilic material that does not pass non-water based liquids or gas. The housing 36 includes a filter portion 44, with a recess 46 for the filter 38, and a connector portion 48 with an outlet lumen 50 that is operably connected to the inlet of the fluid transfer device. A lumen 52 extends from the recess 46 to the outlet lumen 50. The outer perimeter of the filter 38 (i.e., the outer perimeters of the filtration element 40 and support disk 42) is compressed between a support ring 54 and an annular abutment 56 within the recess 46. The support ring 54 may be welded or otherwise secured to the housing filter portion 44.

The internal wall 16 includes an aperture 58 in which the housing filter portion 44 is mounted. The internal wall 16 also includes a recess 60 for the similarly-shaped filter flange 62, which together ensure that that filter housing connector portion 48 is in its intended location within the sealed volume defined by the housing internal wall 16 and cover 18. The respective sizes and configurations of the internal wall 16 and the filter housing 36 results in the free end 64 of the filter housing being flush with the inner surface 66 of the wall 16. Operation of the fluid transfer device causes infusible substance IS within the reservoir internal volume 22 to be draw through the filter 38, recess 46, and lumens 50 and 52, and then into the fluid transfer device inlet. The reservoir convolutes 23 will compress, and the reservoir end wall 24 will move toward the internal wall 16, as the infusible substance is evacuated from the reservoir 20 and the internal volume 22 shrinks.

Although useful, the present inventors have determined that infusion device 10 is susceptible to improvement. One issue is associated with gas bubbles within the reservoir 20 and the configuration of the filter assembly 30. In particular, many infusible substances contain dissolved gases that may evolve from solution and, due to gravity, accumulate and form a bubble at the top region of the reservoir. The region of the reservoir that defines the "top" region will vary based on the orientation of the patient (i.e., standing, sitting, lying down, etc.). With respect to the configuration of the filter assembly 30, and referring to FIGS. 3 and 4, the respective sizes and configurations of the filter housing 36 and filter 38 are such that there is an open, unfilled disk-shaped space (or "pocket") 68 that faces the reservoir internal volume 22. The depth D1 of the pocket 68 is equal to the depth D2 of the portion of the housing recess 46 that extends from the annular abutment 56 to the free end 64, less the thickness of the filter 38. Put another way, the depth D1 of the pocket 68 is equal to distance between the surface of the filter 38 that faces the reservoir and the free end 64 of the housing filter portion 44. The pocket 68 can act as a bubble trap which, as a result of the typical orientation of the infusion device 10 within the patient, will define the highest point within the reservoir when the patient is in a supine position.

The presence of a gas bubble within the pocket 68 and over the filter 38 is problematic because the hydrophilic filter element 40 will be blocked by the bubble. Even a microscopic gas bubble is capable of thinning out, spreading across the entire surface of the wetted filter, thereby preventing the infusible substance from reaching the fluid transfer device. Depending upon the volume of the bubble and negative pressure generated by the pump, the bubble may cover the surface of the support disk 42, and/or fill the perforations of the support disk, and/or or get between the bacterial filtration element 40 and the support disk and cover the reservoir-facing surface of the filtration element. In those instances where the fluid transfer is capable of generating enough force to draw a bubble through the filter 38, certain types of fluid transfer devices (e.g., electromagnet pumps) will experience vapor lock. Moreover, given the depth of the pocket 68 and other factors (e.g., surface tension), the bubble may not float out of the pocket in response to movement and/or reorientation of the patient.

There are also other instances, based on patient orientation and reservoir volume, where the bubble may enter the filter assembly pocket 68. For example, the liquid volume to bubble volume ratio will be relatively large, and the bubble will tend to remain within the bellows convolutes 23, when the reservoir is relatively full (FIG. 2). As the reservoir 20 is depleted, the bubble may be squeezed out of reservoir convolutes 23, and towards the filter assembly 30. A bubble may also simply migrate along the inner surface 66 of the wall 16 toward the filter assembly 30, regardless of reservoir volume, in response to changes in patient (and infusion device) orientation. The present inventors have determined that, in either case, the fact that the free end 64 of the filter housing 44 is flush with the inner surface 66 of the wall 16 increases the likelihood that the bubble will enter the pocket 68.

One example of an implantable infusion device in accordance with at least some of the present inventions is generally represented by reference numeral 100 in FIGS. 5-8. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, a divider wall 106, and a cover 108. An infusible substance (e.g. medication) may be stored in a reservoir 110 that is located within the housing bottom portion 104. The reservoir 110 may be replenished by way of a fill port 112 that extends from the reservoir, through the divider wall 106, to the cover 108. A hypodermic needle (not shown), which is configured to be pushed through the fill port 112, may be used to replenish the reservoir 110. An inlet side safety valve 114, closes when the pressure within the reservoir reaches a predetermined level, may be located between reservoir 110 and the fill port 112.

A wide variety of reservoirs may be employed. In the illustrated embodiment, the reservoir 110 is in the form of a titanium bellows with convolutes 116 and an end wall 118 that is positioned within a sealed volume 120 defined by the housing bottom portion 104 and divider wall 106. The remainder of the sealed volume is occupied by propellant (not shown), which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 100 illustrated in FIGS. 5-8 also includes a fluid transfer device 122 which, in the illustrated implementation, is an electromagnet-pump-based fluid transfer device. Although the present inventions are not so limited, various examples of suitable fluid transfer devices are illustrated and described in U.S. Pat. No. 8,740,861, which is incorporated by reference. The inlet of the fluid transfer device 122 is coupled to the interior 124 (FIGS. 9 and 12) of the reservoir 110 by a filter assembly 126 that is connected to an inlet tube associated with the fluid transfer device 122. The outlet of the fluid transfer device is coupled to an outlet port 128 by a passageway 130 that defines a path from the fluid transfer device to the outlet port. Operation of the fluid transfer device 100 causes infusible substance to move from the reservoir 110 to the infusion device outlet port 128. A catheter 132 may be connected to the outlet port 128 so that the infusible substance passing through the outlet port will be delivered to a target body region in spaced relation to the infusion device 100 by way of the outlet(s) 134 at or near the end of the catheter.

Figure 6:
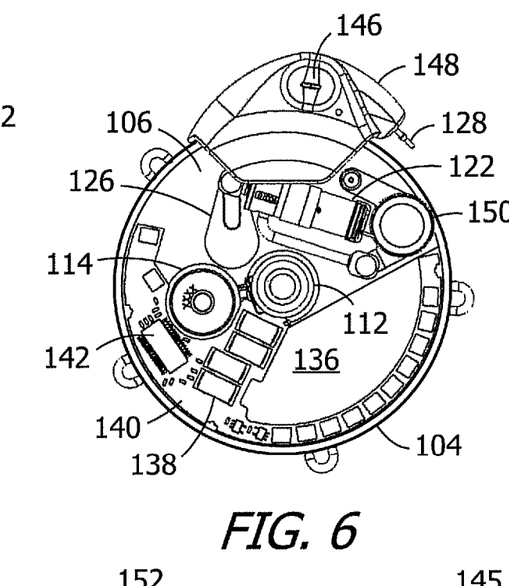
FIG. 6 is a front view of the implantable infusion device illustrated in FIG. 5 with the housing cover removed.
Figure 7:
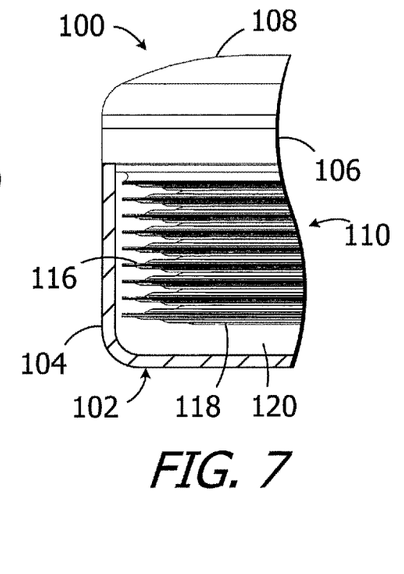
FIG. 7 is a side, partial section view of a portion of the implantable infusion device illustrated in FIG. 5.

Energy for the fluid transfer device 122, as well for other aspects of the exemplary infusion device 100, is provided by the battery 136 illustrated in FIG. 6. In the specific case of the fluid transfer device 100, the battery 136 is used to charge one or more capacitors 138, and is not directly connected to the fluid transfer device itself. The capacitor(s) 138 are connected to an electromagnet coil in the fluid transfer device 122, and disconnected from the battery 136, when the electromagnet coil is being energized, and are disconnected from the electromagnet coil and connected to the battery when the capacitor(s) are being recharged and/or when the fluid transfer device is at rest. The capacitor(s) 138 are carried on a board 140. A communication device 142, which is connected to an antenna (not shown), is carried on the same side of the board 140 as the capacitor(s) 138. The exemplary communication device 142 is an RF communication device. Other suitable communication devices include, but are not limited to, oscillating magnetic field communication devices, static magnetic field communication devices, optical communication devices, ultrasound communication devices and direct electrical communication devices.

A controller 144 (FIG. 8), such as a microprocessor, microcontroller or other control circuitry, is carried on the other side of the board 140. The controller 144 performs the function of controlling the operations of the infusion device 100 in accordance with instructions stored in memory 145 and/or provided by an external device (e.g. a remote control programmer) by way of the communication device 142. For example, the controller 144 may be used to control the fluid transfer device 122 to supply fluid to the patient in accordance with, for example, a stored basal delivery profile or a bolus delivery request. The controller 144 may also be used to monitor sensed pressure and to perform various analytical and corrective functions.

Figure 5:
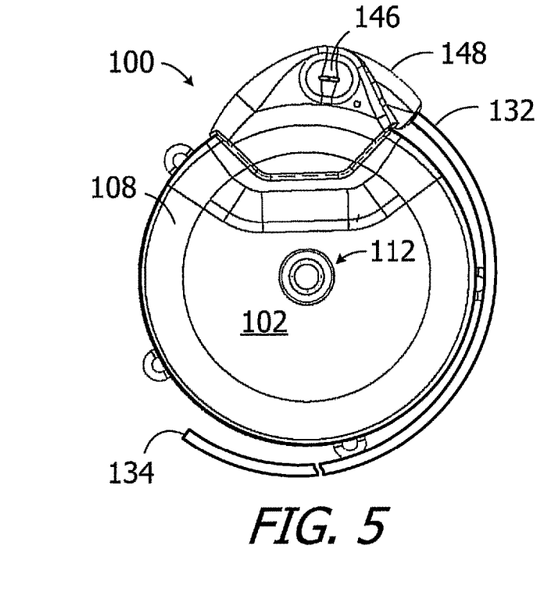
FIG. 5 is a front view of an implantable infusion device in accordance with one embodiment of a present invention.
Figure 8:
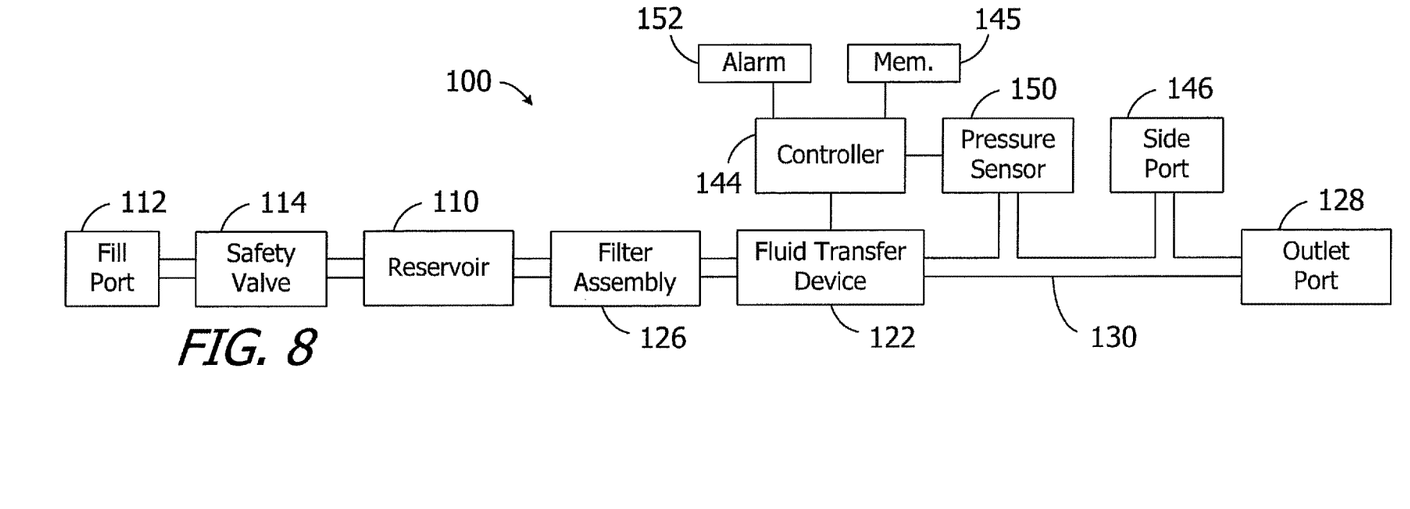
FIG. 8 is a block diagram of the implantable infusion device illustrated in FIG. 5.

Referring to FIGS. 5, 6 and 8, the exemplary infusion device 100 is also provided with a side port 146 that is connected to the passageway 130 between the outlet of the fluid transfer device 122 and the outlet port 128. The side port 146 facilitates access to an implanted catheter 132, typically by way of a hypodermic needle. The outlet port 128, a portion of the passageway 130, the antenna (not shown) and the side port 146 are carried by a header assembly 148. The header assembly 148 is a molded, plastic structure that is secured to the housing 102.

The exemplary infusion device 100 illustrated in FIGS. 5-8 also includes a pressure sensor 150 that is connected to the passageway 130 between the outlet of the fluid transfer device 122 and the outlet port 128. The pressure sensor 150 is connected to the controller 144 and may be used to analyze a variety of aspects of the operation of the exemplary implantable infusion device 100. For example, pressure measurements may be used by the controller 144 to determine whether or not there is a blockage in the catheter 132 and whether or not the fluid transfer device 122 is functioning properly. The controller 144 may perform a variety of different functions in response to a determination that the fluid transfer device 122 is not functioning properly or a determination that the catheter 132 is blocked. For example, the controller 144 may actuate an audible alarm 152 that is located within the housing 102 in order to signal that the fluid transfer device 122 is not functioning properly or the catheter 132 is blocked. The controller 144 may also be used to determine, based on the pressure sensed by the pressure sensor 150, whether there is a blockage.

Turning to FIGS. 9-12, the exemplary filter assembly 126 includes a housing 154, a filter 156 having a hydrophilic bacterial filter element 158 and a perforated support disk 160 (or other liquid permeable filter support) that prevents distortion of the filter element, and a bubble guard 162. Suitable materials for the filter element 158 and other filter elements discussed herein include, but are not limited to polysulfone, polyvinylidene fluoride, and cellulose with a thickness of about 125 µm to 200 µm, while suitable materials for the perforated disk 160 and other perforated disks discussed herein include, but are not limited to titanium, stainless steel, polysulfone with a thickness of about 0.1 mm to 5 mm. The disk perforations 164, which extend completely through the disk 160, may be about 0.01 mm to 1 mm in diameter. The perforated disk 160 may be secured to the housing by press fitting, welding, or any other suitable process or instrumentality.

The exemplary housing 154 includes a filter portion 166, with a side wall 167 and an end wall 169 that together define a recess 168 for the filter 156, and a connector portion 170 with an outlet lumen 172 that is operably connected to the inlet of the fluid transfer device 122. A lumen 174 extends from the recess 168 to the outlet lumen 172. The divider wall 106 includes an aperture 176 in which the housing filter portion 166 is mounted as well as a recess 178 for the similarly-shaped filter flange 180, which together ensure that that filter housing connector portion 170 is in its intended location adjacent to the inlet of the fluid transfer device 122.

The exemplary bubble guard 162 includes a wall 182 that is located in spaced relation the filter 156, one or more apertures 184 that extend through the wall, and a mounting flange 186. The exemplary wall 182 has a convex shape and is symmetric about the apex 183. The convex shape may, for example, be a segment of a sphere. The apertures 184 may be circular. Other wall shapes, such as wall shapes that are convex and asymmetric about the apex, or a flat (or "planar") wall shape may also be employed. The number of apertures 184 may be increased or decreased, and the apertures may be circular, as shown, or any other suitable shape. The apertures 184 may also be symmetrically concentrated in the region adjacent to the apex of the convex wall 182, as shown, or may be located over more or less of the wall surface.

The bubble guard 162 reduces the likelihood that bubbles will enter the pocket 157 (FIG. 12) within the housing filter portion 166, and adjacent to the filter 156, that faces the reservoir interior 124. For example, as a result of the convex shape of the wall 182, bubbles will tend to roll off the bubble guard 162 instead of entering the pocket 157 by way of the apertures 184.

Figures 9, 10, 11, 12:
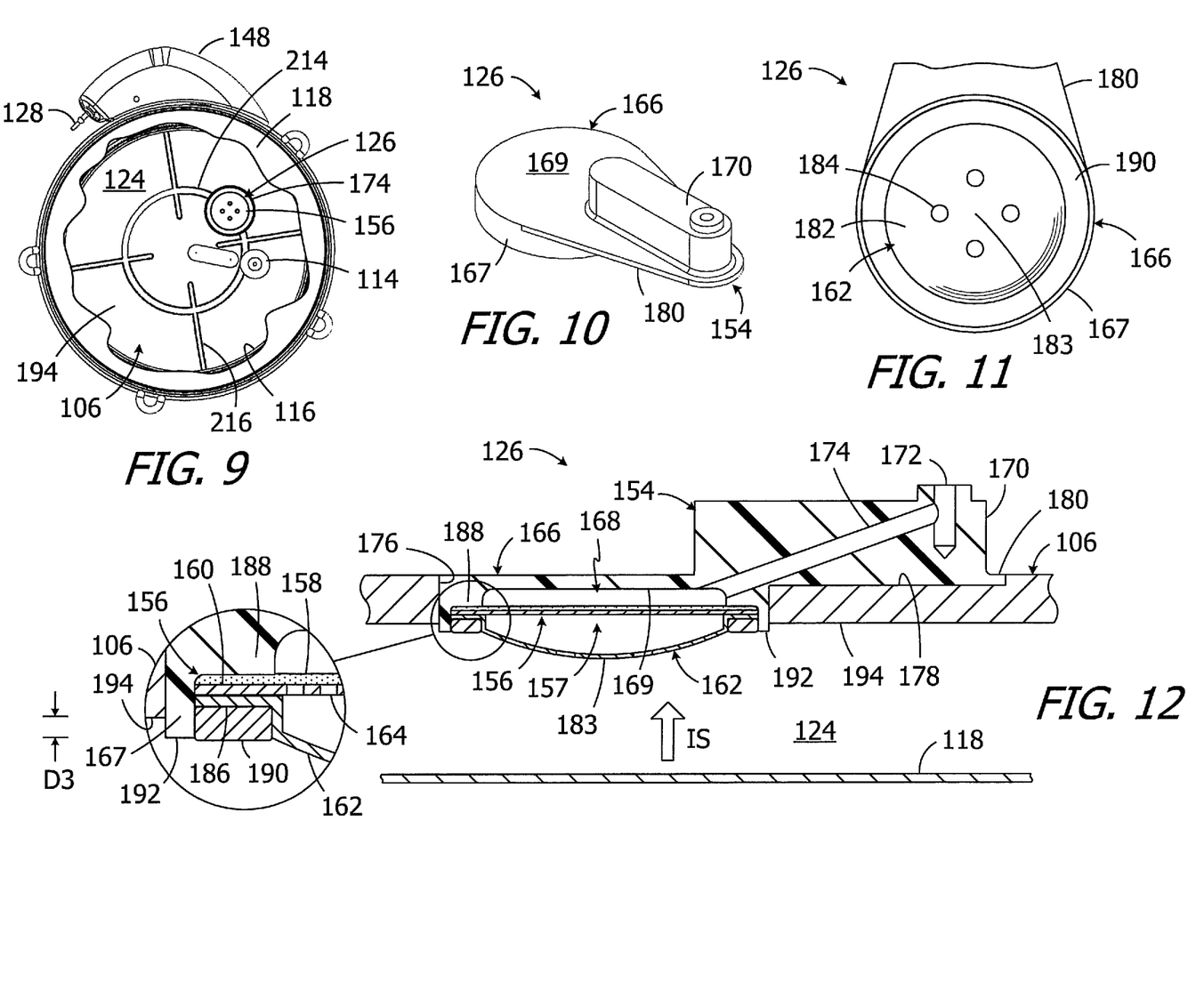
FIG. 9 is a rear, cutaway view of the implantable infusion device illustrated in FIG. 5 with the housing bottom portion removed.
FIG. 10 is a perspective view of the filter assembly in the implantable infusion device illustrated in FIG. 5.
FIG. 11 is a bottom view of the filter assembly in the implantable infusion device illustrated in FIG. 5.
FIG. 12 is a section view of a portion of the implantable infusion device illustrated in FIG. 5.

In the illustrated implementation, the filter 156 and bubble guard 162 are pressed into the filter recess of the housing 154 and are secured thereto. For example, the outer perimeters of the filter element 158 and support disk 160, as well as the mounting flange 186 of the bubble guard 162, may be pressed between an annular abutment 188 within the recess 168 and a support ring 190. The support ring 190 may be welded, press-fit, or otherwise secured to the housing filter portion 166.

It should also be noted that the free end 192 of the housing filter portion 166 is not flush with the inner surface 194 of the divider wall 106 in the illustrated implementation. The free end 192 is instead offset the inner surface 194, which faces and defines a border of the reservoir interior 124, by a distance D3 of about 0.1 mm to 1.0 mm and projects into the reservoir interior by the distance D3. The part of the housing filter portion 166 that extends beyond the inner surface 194 acts as a barrier, or fence, that will impede a bubble within the reservoir interior that is moving along the inner surface of the divider wall 106 prior to the bubble reaching the filter 156.

Turning to FIG. 9, the filter assembly 126 is not located adjacent to the reservoir convolutes 116. As such, a bubble squeezed out of reservoir convolutes 116 and towards the filter assembly 126, as the reservoir interior 124 is depleted, will be less likely to reach the filter assembly and cover the filter 156.

Figures 13, 14:
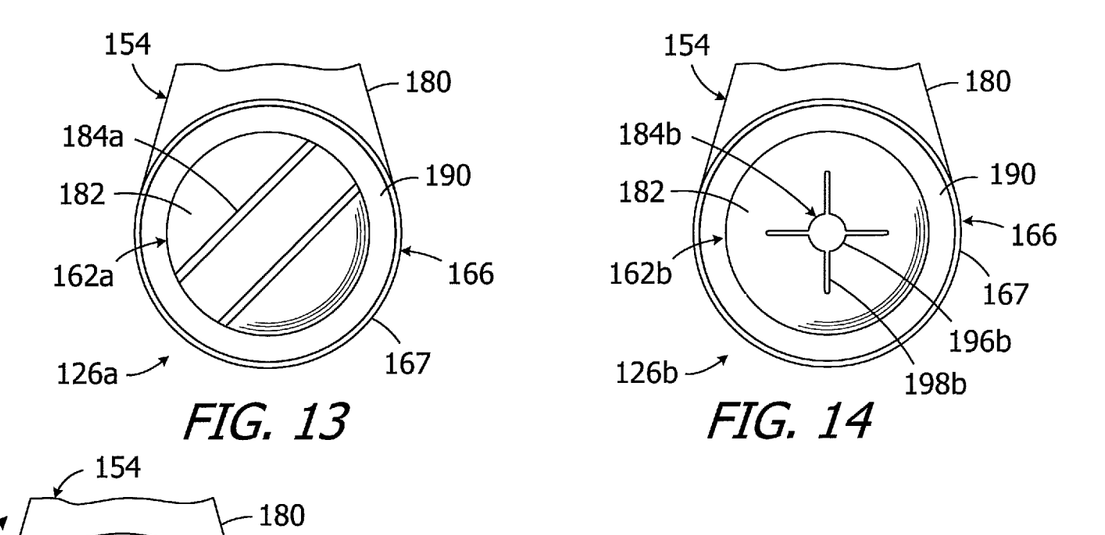
FIG. 13 is a bottom view of a filter assembly in accordance with one embodiment of a present invention.
FIG. 14 is a bottom view of a filter assembly in accordance with one embodiment of a present invention.

Another exemplary filter assembly is generally represented by reference numeral 126a in FIG. 13. The exemplary filter assembly 126a is substantially similar to filter assembly 126 and similar elements are represented by similar reference numerals. For example, the filter assembly 126a may be incorporated into the exemplary infusion device 100 in place of the filter assembly 126. The filter assembly 126a includes the housing 154 and filter 156 described above with reference to FIGS. 9-12 as well as a bubble guard 162a with a wall 182 and a mounting flange (not shown). The wall 182 may be convex and symmetric, as shown, or one of the other shapes described above and below. Here, however, the bubble guard 162a includes one or more narrow linear slots 184a that extend through the wall 182 in place of the aforementioned circular apertures 184. The slots 184a may extend completely across the wall 182, i.e., from one portion of the support ring 190 to another, as shown, or only partially across the wall. The slots 184a may also be linear, as shown, or curved. In still other implementations, one or more circular apertures 184 may be combined with one or more slots 184a.

Turning to FIG. 14, the exemplary filter assembly 126b is substantially similar to filter assembly 126 and similar elements are represented by similar reference numerals. For example, the filter assembly 126b may be incorporated into the exemplary infusion device 100 in place of the filter assembly 126. The filter assembly 126b includes the housing 154 and filter 156 described above with reference to FIGS. 9-12 as well as a bubble guard 162b with a wall 182 and a mounting flange (not shown). The wall 182 may be convex and symmetric, as shown, or one of the other shapes described above and below. Here, however, the aperture 184b that extends through the wall 182 includes a central portion 196b and a plurality of slots 198b that extend outwardly from the central portion. The central portion 196b may be circular, as shown, or another shape. The slots 184b may extend part way to the support ring 190, as shown, or all the way to the support ring. The slots 184b may also be linear, as shown, or curved, and the number of slots may be increased or decreased.

Figure 15:
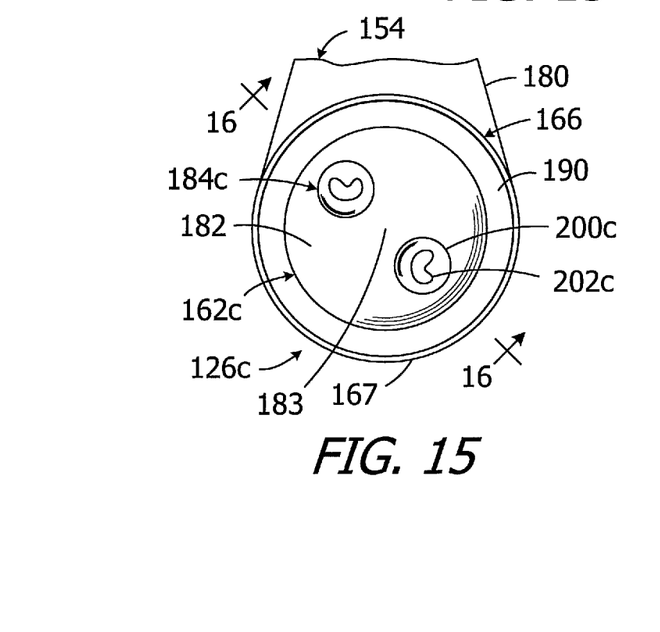
FIG. 15 is a bottom view of a filter assembly in accordance with one embodiment of a present invention.
Figure 16:
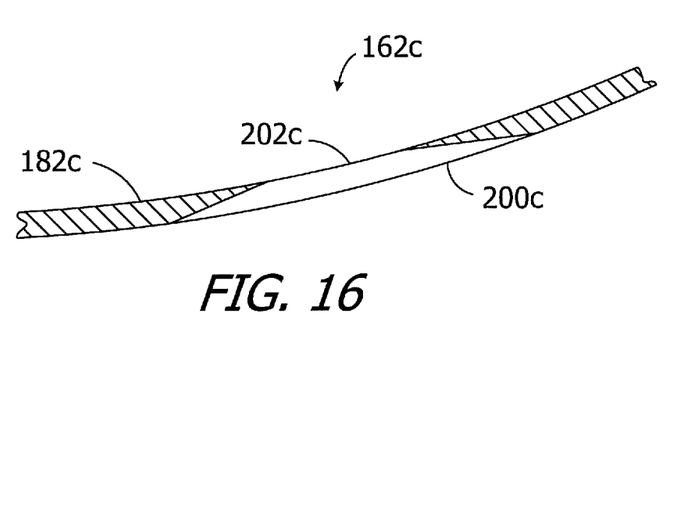
FIG. 16 is a section view taken along line 16-16 in FIG. 15.

Referring to FIGS. 15 and 16, the exemplary filter assembly 126c is substantially similar to filter assembly 126 and similar elements are represented by similar reference numerals. For example, the filter assembly 126c may be incorporated into the exemplary infusion device 100 in place of the filter assembly 126. The filter assembly 126c includes the housing 154 and filter 156 described above with reference to FIGS. 9-12 as well as a bubble guard 162c with a wall 182 and a mounting flange (not shown). The wall 182 may be convex and symmetric, as shown, or one of the other shapes described above and below. Here, however, the bubble guard 162c includes one or more tapered apertures 184c that extend through the wall 182 in place of the aforementioned circular apertures 184. The apertures 184c taper downwardly from a circular outer end 200c to an irregular inner end 202c. In the illustrated embodiment, the irregular inner end 202c has a "kidney bean" shape. Although the illustrated embodiment includes two apertures 184c that are equidistant from the apex 183 of the convex wall 182, the number of apertures 184c may be increased or decreased, and/or the apertures may be different distances from the apex of the convex wall.

Figure 17:
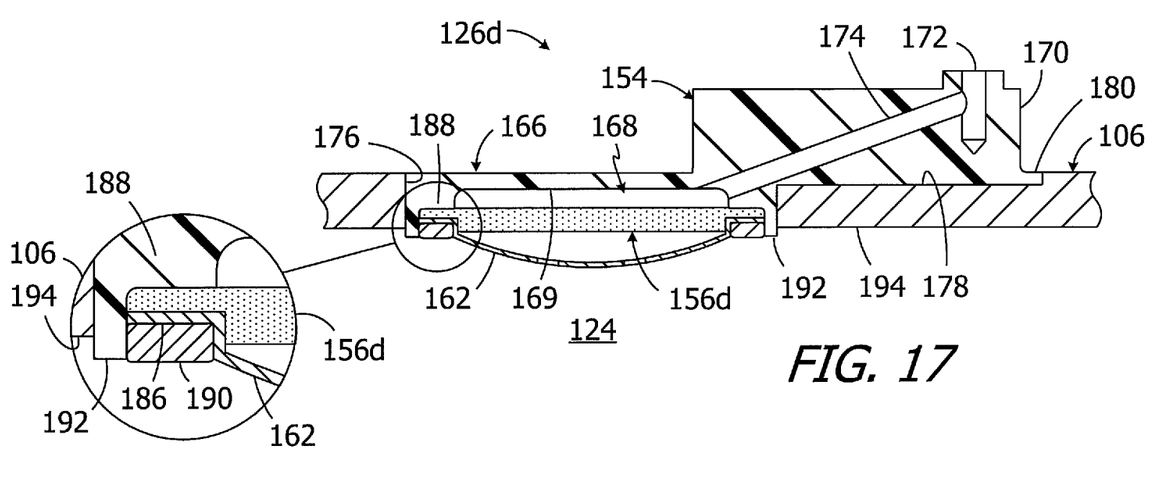
FIG. 17 is a section view of a portion of an implantable infusion device in accordance with one embodiment of a present invention.
Figure 17A:
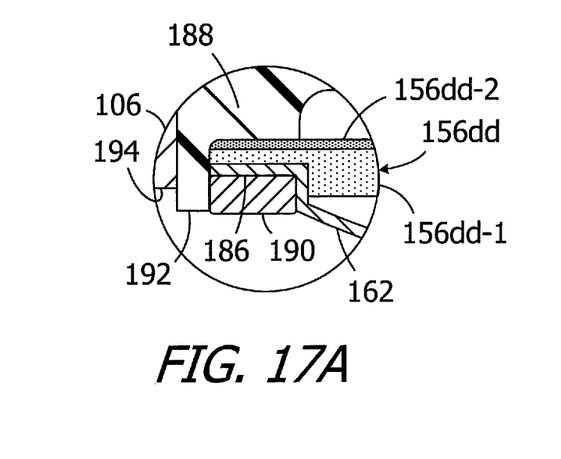
FIG. 17A is a section view of a portion of an implantable infusion device in accordance with one embodiment of a present invention.

Turning to FIG. 17, the exemplary filter assembly 126d is substantially similar to filter assembly 126 and similar elements are represented by similar reference numerals. For example, the filter assembly 126d may be incorporated into the exemplary infusion device 100 in place of the filter assembly 126. The filter assembly 126d includes the housing 154 and bubble guard 162. Here, however, the filter 156d is an integrated, unitary structure. For example, the filter 156d may consist of a hydrophilic membrane that is laminated to one or more layers of support material. Exemplary hydrophilic membranes may be formed from materials such as polysulfone, while exemplary support materials include woven or non-woven polypropylenes and polyesters or a calendered support. The outer perimeter of the filter 156c is compressed between the bubble guard mounting flange 186 and the annular abutment 188. In other embodiments, the integrated, unitary structure may be formed from porous sintered titanium (or other porous sintered metal). Such a porous sintered metal filter may have, for example, an absolute filter rating (or "filter rating") of 0.2 µm, i.e., the filter will block particles that are 0.2 µm or larger. The filter rating is may be consistent throughout the filter, or may vary over the thickness of the filter. To that end, the exemplary filter 156dd (FIG. 17A), which may be used in place of the filter 156d in the filter assembly 126d, includes a first filter layer 156dd-1 with a filter rating of 0.2 µm and a second filter layer 156dd-2 with a filter rating of 2.0 µm. In other implementations, the filter rating variation may be gradual over the entire thickness, as opposed to the use of two distinct layers having different filter ratings.

Figure 18:
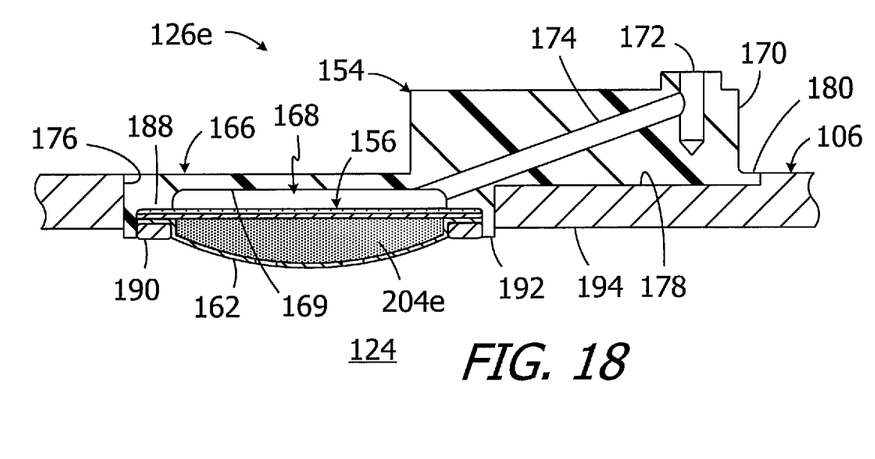
FIG. 18 is a section view of a portion of an implantable infusion device in accordance with one embodiment of a present invention.

Referring to FIG. 18, the exemplary filter assembly 126e is substantially similar to filter assembly 126 and similar elements are represented by similar reference numerals. For example, the filter assembly 126e may be incorporated into the exemplary infusion device 100 in place of the filter assembly 126. The filter assembly 126e also includes the housing 154, filter 156, and bubble guard 162. Here, however, a liquid absorbent member 204e is located between the filter 156 and bubble guard 162. The liquid absorbent member 204e stores the infusible substance. In the unlikely event that all of the bubble guard apertures 184 are completely covered by a bubble, the infusible substance stored in the liquid absorbent member 204e will be drawn through the filter 156, and into the fluid transfer device 122, until the bubble moves. Suitable materials for the liquid absorbent member 204e include, but are not limited to hydrophilic sponge materials, polyurethane, and cellulose. The liquid absorbent member 204e may fill the entire volume between the filter 156 and bubble guard 162, as shown, or may fill less than the entire volume. It should also be noted that the liquid absorbent member 204e may be used in conjunction with any of the filter assemblies described herein.

Figure 19:
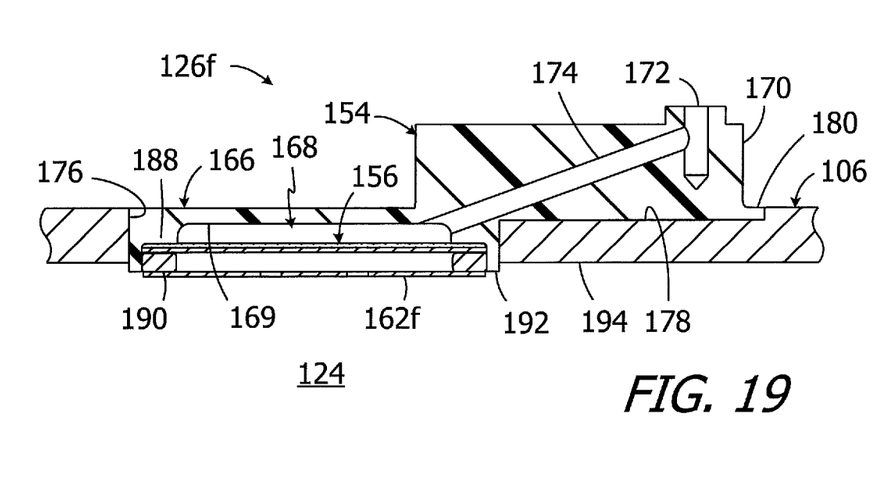
FIG. 19 is a section view of a portion of an implantable infusion device in accordance with one embodiment of a present invention.
Figure 20:
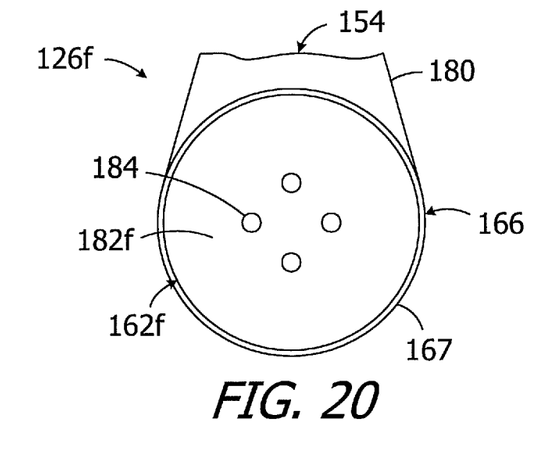
FIG. 20 is a bottom view of the filter assembly illustrated in FIG. 19.

Another exemplary filter assembly is generally represented by reference numeral 126f in FIGS. 19 and 20. The exemplary filter assembly 126f is substantially similar to filter assembly 126 and similar elements are represented by similar reference numerals. For example, the filter assembly 126f may be incorporated into the exemplary infusion device 100 in place of the filter assembly 126. The filter assembly 126f includes the housing 154 and filter 156 described above with reference to FIGS. 9-12 as well as a bubble guard 162f with a wall 182f and a plurality of apertures 184. Here, however, the bubble guard wall 182f is flat and is mounted on the support ring 190 in such a manner that the bubble guard 162f is separated from the filter 156 by the support ring 190. The number of apertures 184 may be increased or decreased, and the apertures may be circular, as shown, or any other suitable shape. For example, the aperture configurations described above with reference to the embodiments illustrated in FIGS. 13-16 may also be employed on a flat bubble guard. The apertures 184 may also be symmetrically concentrated in the region adjacent to the center of the flat wall 182f, as shown, or may be located over more or less of the wall surface.

Figure 21:
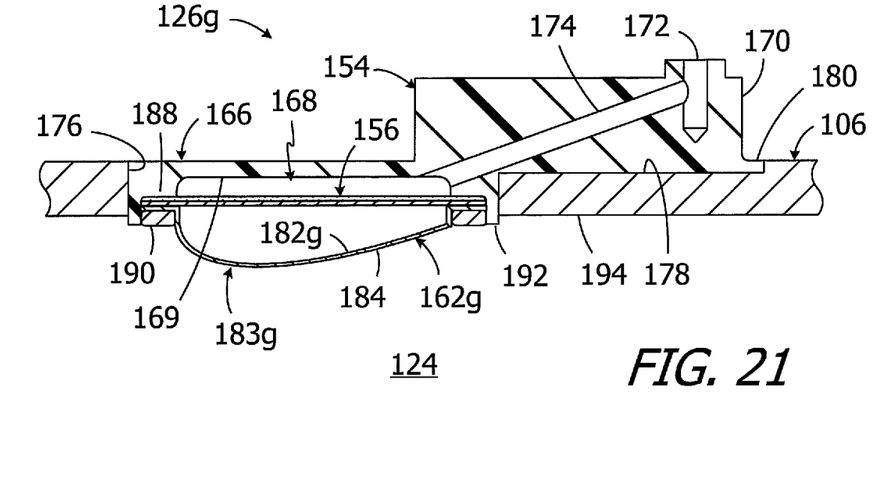
FIG. 21 is a section view of a portion of an implantable infusion device in accordance with one embodiment of a present invention.
Figure 22:
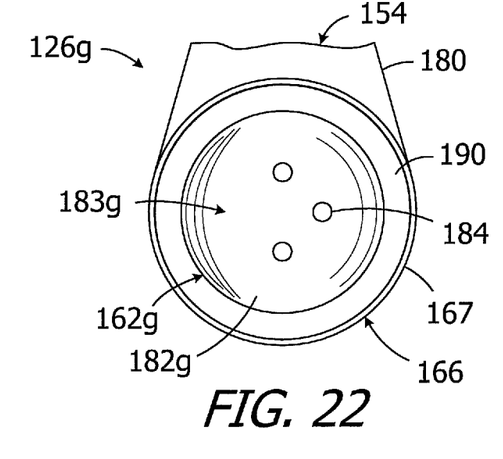
FIG. 22 is a bottom view of the filter assembly illustrated in FIG. 21.

Turning to FIGS. 21 and 22, the exemplary filter assembly 126g is substantially similar to filter assembly 126 and similar elements are represented by similar reference numerals. For example, the filter assembly 126g may be incorporated into the exemplary infusion device 100 in place of the filter assembly 126. The filter assembly 126g includes the housing 154, the filter 156 described above with reference to FIGS. 9-12, and a bubble guard 162g with a convex wall 182g and a plurality of apertures 184. Here, however, the bubble guard wall 182g is asymmetric, i.e., the apex 183g is not centered relative to the outer perimeter of the bubble guard wall. In the illustrated implementation, the apertures 184 are only located on the portion of the wall 182g that slopes gradually from the apex 183g to the support ring 190, i.e., the portion of the wall to the right of the apex in the illustrated orientation, and there are no apertures on the other side of the apex. The bubble guard 162g may be oriented relative to the filter assembly 126g (and remainder of the infusion device), and the infusion device may be oriented within the patient, in such a manner that the portion of the wall 182g with no apertures will face upwardly when the patient is standing. As a result, bubbles (if any) will congregate on a portion of the wall 182g away from the apertures 184. The number of apertures 184 may be increased or decreased, and the apertures may be circular, as shown, or any other suitable shape. For example, the aperture configurations described above with reference to the embodiments illustrated in FIGS. 13-16 may also be employed on a asymmetric bubble guard.

Figure 23:
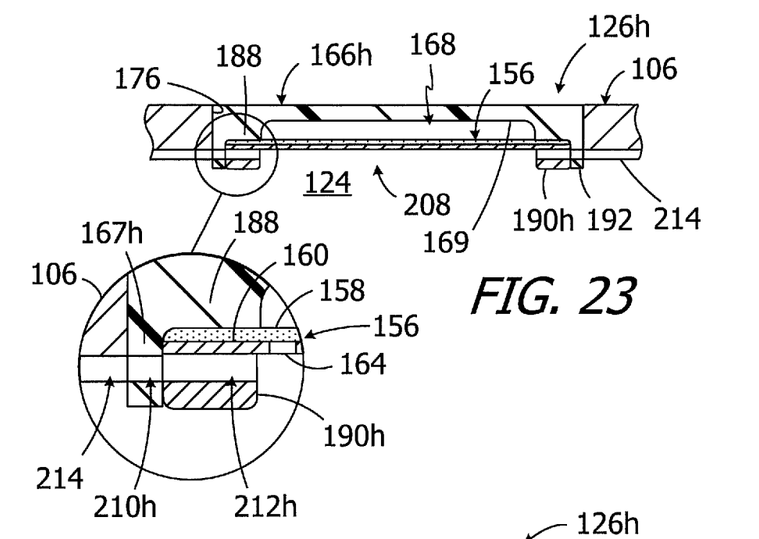
FIG. 23 is a section view of a portion of an implantable infusion device in accordance with one embodiment of a present invention.
Figure 24:
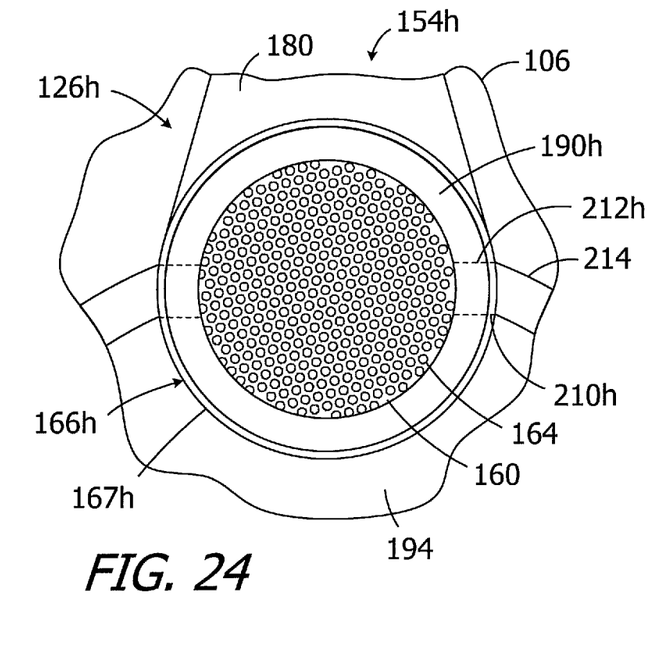
FIG. 24 is a bottom view of the portion of an implantable infusion device illustrated in FIG. 23.
Figure 25:
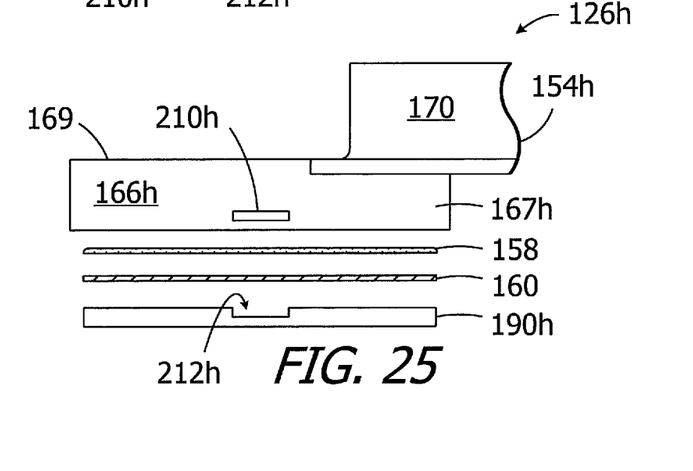
FIG. 25 is an exploded view the filter assembly illustrated in FIG. 23.

Other filter assemblies in accordance with present inventions may be configured in such a manner that fluid may reach the filter despite the presence of a bubble over the filter. By way of example, but not limitation, the exemplary filter assembly 126h illustrated in FIGS. 23-25 is substantially similar to filter assembly 126 and similar elements are represented by similar reference numerals. For example, the filter assembly 126h may be incorporated into the exemplary infusion device 100 in place of the filter assembly 126. The filter assembly 126h includes a housing 154h and the filter 156 described above with reference to FIGS. 9-12. Here, however, the bubble guard has been omitted and the housing 154h is configured to permit the infusible substance with the reservoir interior 124 to pass through the side wall 167h of the housing filter portion 166h and under the outer perimeter of a bubble that is located within the pocket 208, i.e., a bubble that is located under the filter 156 and within the inner perimeter of the side wall, as is described below with reference to FIG. 26. In the illustrated implementation, the side wall 167h includes one or more apertures 210h (e.g., two) that extend from the inner surface of the side wall to the outer surface, and the support ring 190h includes one or more grooves 212h (e.g., two) on the side that abuts the perforated support disk 160. The apertures 210h and grooves 212h are aligned with one another and together define a lateral flow path for the infusible substance. The lateral flow paths extend from the outer surface of the side wall 167h to the outer perimeter of the pocket 208 where the support ring 190h abuts the filter 156.

In some implementations, and referring to FIG. 9, the inner surface 194 of the divider wall 106 may include one or more channels, such as channels 214 and 216, which prevent the bellows end wall 118 from sticking to the divider wall 106 when the reservoir is empty. The channels 214 and 216 also provide an infusible substance flow path under a bubble, and to the filter assembly 126h, in those instances where a bubble is located on the divider wall 106 adjacent to the filter assembly. Here, the apertures 210h and grooves 212h will be aligned with the channel 214, as shown in FIGS. 23 and 24. The channels 214 and/or 216 may in some instances be coated with, or filled with, liquid absorbent material (such as, for example, hydrophilic sponge materials, polyurethane, and cellulose) to enhance the flow path defined by the channels and to deter bubble formation within the channels.

Figure 26:
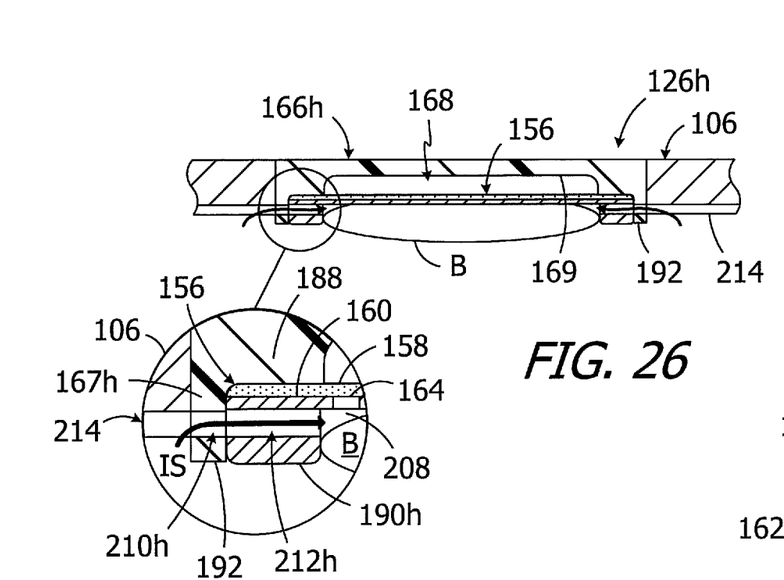
FIG. 26 is a section view of the portion of an implantable infusion device illustrated in FIG. 23 and a bubble.

Turning to FIG. 26, the apertures 210h and grooves 212h provide an alternate flow path for the infusible substance IS that does not require the infusible substance to enter pocket 208 of the filter assembly 126h by way of the opening that is defined by the inner diameter of the support ring 190h. Instead, the flow path defined by the apertures 210h and grooves 212h allows the infusible substance to enter the pocket 108 at the outer perimeter of the pocket and under the outer perimeter of the bubble B. In other words, the infusible substance flows into the between the filter 156 and the outer perimeter of the bubble B.

Figure 27:
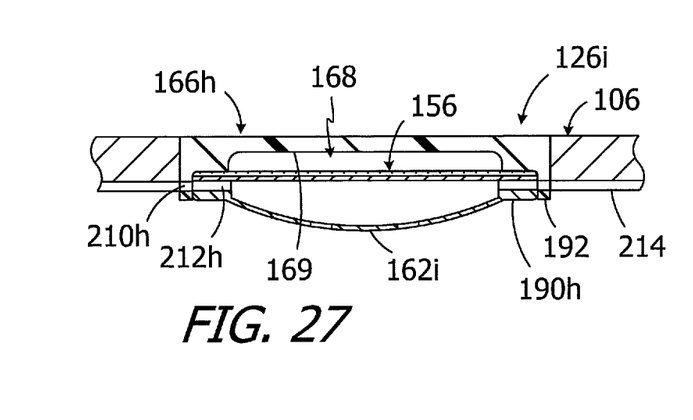
FIG. 27 is a section view of a portion of an implantable infusion device in accordance with one embodiment of a present invention.
Figure 28:
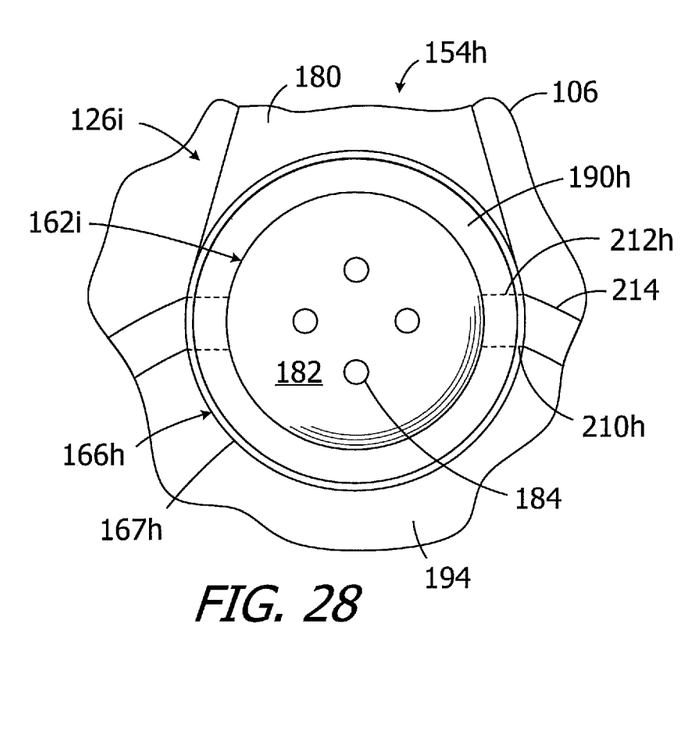
FIG. 28 is a bottom view of the portion of an implantable infusion device illustrated in FIG. 27.

Another exemplary filter assembly is generally represented by reference numeral 126i in FIGS. 27 and 28. Filter assembly 126i is substantially similar to filter assembly 126h and similar elements are represented by similar reference numerals. For example, the filter assembly 126i, which may be incorporated into the exemplary infusion device 100 in place of the filter assembly 126h, includes apertures 210h and grooves 212h that together define an alternate flow path the infusible substance. Here, however, a bubble guard 162i is also provided. The bubble guard 162i has a similar configuration as the bubble guard 162 in that it includes a convex wall 182 and apertures 184, does not include a mounting flange 186 (FIG. 12). Instead, the bubble guard wall 182 is secured (e.g., by welding) directly to the support ring 190h. Any of the other wall and aperture configurations described above may also be employed.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. Moreover, the inventions include any and all combinations of the elements from the various embodiments disclosed in the specification. It is intended that the scope of the present inventions extend to all such modifications and/or additions and that the scope of the present inventions is limited solely by the claims set forth below.

We claim:

1. An ambulatory infusing device, comprising:
a housing;
a reservoir having an end wall and defining an interior volume;
a divider wall associated with the housing, located a first distance from the reservoir end wall, and having an inner surface that faces into the reservoir interior volume; and
a filter assembly including
a filter assembly housing with a housing filter portion having a filter supporting volume,
a filter located within the filter supporting volume, and
a bubble guard, including a bubble guard wall and at least one bubble guard aperture that extends through the bubble guard wall, associated with the filter assembly housing such that the bubble guard wall is located in spaced relation to the filter and the at least one bubble guard aperture is located a second distance from the reservoir end wall that is less than the first distance.

2. An ambulatory infusing device as claimed in claim 1, wherein the filter comprises a filter element and a liquid permeable filter support.

3. An ambulatory infusing device as claimed in claim 2, wherein the filter element comprises a hydrophilic membrane.

4. An ambulatory infusing device as claimed in claim 2, wherein the liquid permeable filter support comprises a perforated disk.

5. An ambulatory infusing device as claimed in claim 2, wherein the filter element is laminated to the liquid permeable filter support.

6. An ambulatory infusing device as claimed in claim 1, wherein the filter comprises a sintered metal filter.

7. An ambulatory infusing device as claimed in claim 6, wherein different portions of the sintered metal filter define different filter ratings.

8. An ambulatory infusing device as claimed in claim 1, further comprising:
a liquid absorbent member located between the filter and the bubble guard.

9. An ambulatory infusing device as claimed in claim 1, wherein the bubble guard wall comprises a convex bubble guard wall.

10. An ambulatory infusing device as claimed in claim 9, wherein the convex bubble guard wall defines an apex and is symmetric about the apex.

11. An ambulatory infusing device as claimed in claim 9, wherein the convex bubble guard wall defines an apex and is asymmetric about the apex.

12. An ambulatory infusing device as claimed in claim 9, wherein
the convex bubble guard wall defines an apex; and
the apex of the convex bubble guard wall extends into the reservoir interior volume and beyond the inner surface of the divider wall.

13. An ambulatory infusing device as claimed in claim 1, wherein the bubble guard wall comprises a flat bubble guard wall.

14. An ambulatory infusing device as claimed in claim 1, wherein
the filter assembly housing includes a side wall and a filter assembly end wall that define the filter supporting volume; and
the side wall includes a side wall aperture that extends through the side wall to the filter supporting volume.

15. An ambulatory infusing device as claimed in claim 14, wherein
- the inner surface of the divider wall includes a channel; and
- the side wall aperture is aligned with the channel.

16. An ambulatory infusing device as claimed in claim 1, wherein
- the bubble guard aperture is selected from the group consisting of
  - a circular aperture,
  - a slot,
  - an aperture having a central portion and a plurality of slots that extend outwardly from the central portion, and
  - a tapered aperture having a circular outer end and an irregular inner end.

17. An ambulatory infusing device as claimed in claim 1, wherein the at least one bubble guard aperture comprises a plurality of bubble guard apertures.

18. An ambulatory infusing device as claimed in claim 1, wherein the reservoir comprises a bellows reservoir.

19. An ambulatory infusing device as claimed in claim 1, further comprising:
- a fluid transfer device operably connected to the reservoir interior volume by way of the filter assembly.

20. An ambulatory infusing device as claimed in claim 1, wherein the fluid transfer device comprises an electromagnet pump-based fluid transfer device.

\* \* \* \* \*